United States Patent
Hata et al.

(10) Patent No.: US 10,058,571 B2
(45) Date of Patent: Aug. 28, 2018

(54) FIBROSIS-CAUSING AGENT

(71) Applicant: Terumo Kabushiki Kaisha, Tokyo (JP)

(72) Inventors: Suguru Hata, Kanagawa (JP); Yuichi Tada, Kanagawa (JP); Ayaka Akutagawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 33 days.

(21) Appl. No.: 15/454,681

(22) Filed: Mar. 9, 2017

(65) Prior Publication Data

US 2017/0173081 A1    Jun. 22, 2017

Related U.S. Application Data

(62) Division of application No. 14/463,139, filed on Aug. 19, 2014.

(30) Foreign Application Priority Data

Aug. 13, 2013 (JP) .................. 2013-169747

(51) Int. Cl.
A61K 35/19 (2015.01)
A61K 31/734 (2006.01)
A61K 9/00 (2006.01)
A61K 35/16 (2015.01)
A61K 38/36 (2006.01)
A61K 38/48 (2006.01)
A61K 45/06 (2006.01)
A61K 47/02 (2006.01)

(52) U.S. Cl.
CPC .............. *A61K 35/19* (2013.01); *A61K 9/007* (2013.01); *A61K 31/734* (2013.01); *A61K 35/16* (2013.01); *A61K 38/363* (2013.01); *A61K 38/4833* (2013.01); *A61K 45/06* (2013.01); *A61K 47/02* (2013.01)

(58) Field of Classification Search
None
See application file for complete search history.

(56) References Cited

U.S. PATENT DOCUMENTS

| | | |
|---|---|---|
| 2003/0152639 A1 | 8/2003 | Britton et al. |
| 2003/0228344 A1 | 12/2003 | Fields et al. |
| 2007/0110813 A1 | 5/2007 | Ingenito et al. |
| 2012/0087988 A1 | 4/2012 | Gold |

FOREIGN PATENT DOCUMENTS

| | | |
|---|---|---|
| JP | 2009-514860 A | 4/2009 |
| JP | 514860 A | 4/2009 |
| JP | 501813 A | 1/2012 |
| JP | 2012-45358 A | 3/2012 |
| WO | 2010030993 A1 | 3/2010 |

OTHER PUBLICATIONS

Japanese office action of Japanese patent application 2013-169747, dated Jan. 24, 2017, p. 4.
English abstract of JP2012-45358, Mar. 8, 2012, p. 2.
English abstract of JP2009-514860, Apr. 9, 2009, p. 1.
Marx, Robert E; "Platelet-Rich Plasma: Evidence to Support Its Use" Journal of Oral and Maxillofacial Surgery, 62, 489-496, 2004.

*Primary Examiner* — David W Berke-Schlessel

(57) ABSTRACT

A fibrosis-causing agent is highly effective in the fibrosis of tissues. The fibrosis-causing agent contains a fibrosis inducer and a fibrosis promoter. A fibrosis-causing agent dosage form and a method of administering the fibrosis-causing agent is also disclosed.

9 Claims, 10 Drawing Sheets

FIBROSIS-CAUSING AGENT

CROSS REFERENCE TO RELATED APPLICATIONS

This application is a divisional of and claims priority to U.S. application Ser. No. 14/463,139, filed on Aug. 19, 2014, which claims priority to Japanese National Application No. 2013-169747, filed on Aug. 19, 2013, the entire contents of each and every foregoing application are incorporated by reference herein.

BACKGROUND OF THE DISCLOSURE

The present description relates to a fibrosis-causing agent.

Among a large variety of pulmonary diseases which hamper normal respiration is chronic obstructive pulmonary disease (COPD). It includes at least one of asthma, pulmonary emphysema, and chronic bronchitis, which occludes the lung. These diseases often give rise to their symptoms at one time, thereby making it difficult to determine which one of them causes lung occlusion in each case. COPD remains unchanged for several months and hence chronic bronchitis is clinically identified from the continued reduction of expiration for two or more years. The most serious symptoms relating to COPD are chronic bronchitis and pulmonary emphysema.

The pulmonary emphysema is characterized by an extraordinary expansion, accompanied by disorganization, of respiratory bronchioles, pulmonary alveoli, and alveolar sacs, which are collectively called alveolar parenchyma for gas exchange. The alveolar parenchyma in its normal state shrinks at the time of expiration; however, the enlarged alveolar parenchyma does not recover after expansion due to breathing. This prevents satisfactory expiration. Moreover, the pulmonary emphysema decreases the effective area of pulmonary alveoli and the number of capillary vessels running in all directions on the surface of pulmonary alveoli, which reduces the overall ventilating capacity of the lung. In addition, the lung suffering from pulmonary emphysema is poor in resilience and unable to keep the airway open by stretching because it has its elastin and collagen destroyed by inflammation. This makes the bronchus liable to deformation. The result is that as the lung shrinks for expiration the bronchus becomes narrow due to compression by its surrounding air-filled alveoli and the lung excessively expands, thereby preventing smooth expiration. This is the reason why patients with pulmonary emphysema expire breath while keeping their lips pursed up.

In Japan, there are about 50,000 patients with pulmonary emphysema, who receive home oxygen therapy. Moreover, those who are in the incipient or moderate stage of pulmonary emphysema are estimated to count up to about three million. The present medical treatment of pulmonary emphysema relies mostly on drug therapy and oxygen therapy. They are symptomatic therapies intended to alleviate or eliminate the symptom with the help of a bronchodilator which expands the bronchus to aid respiration. They are not necessarily effective. There are other therapies than mentioned above, such surgical ones as lung implantation, lung volume reduction surgery (LVRS), and bronchoscopic volume reduction (BVR). They still have many problems with great burdens on patients, poor prognosis (in the case of lung implantation), the possibility of pulmonary emphysema occurring in the remaining lung (in the case of LVSR), and limited past records proving effectiveness (in the case of BVR).

In contrast with the foregoing therapies, a new therapy we recently designed that reduces the lung capacity in a non-invasive manner. For example, JP-T-2009-514860 discloses a composition containing polycations and polyanions such that the ratio of X to Y is larger than about 1, where X denotes the product of the mass of polycations and the ratio of the electric charge per mass of polycations, and Y denotes the product of the mass of polyanions and the ratio of the electric charge per mass of polyanions. According to the disclosure, the composition promotes the localized pulmonary fibrosis in the lung's affected part, thereby achieving the lung volume reduction (LVR) and curing pulmonary emphysema (or COPD).

SUMMARY OF THE DISCLOSURE

The present inventors found that the composition disclosed in JP-T-2009-514860 does not necessarily achieve fibrosis sufficiently and hence it does not necessarily produce the effect of reducing the lung capacity as desired.

Thus, it is an intention of the present disclosure to provide a fibrosis-causing agent which effectively causes the fibrosis of tissues.

As the result of extensive investigation, the present inventors found that the above-mentioned problems are solved by a new fibrosis-causing agent which contains in combination a fibrosis inducer (which induces fibrosis) and a fibrosis promoter (which promotes fibrosis). This finding has led to the present disclosure.

The present disclosure provides a fibrosis-causing agent which effectively causes the fibrosis of tissues.

DETAILED DESCRIPTION

Figure 1A:
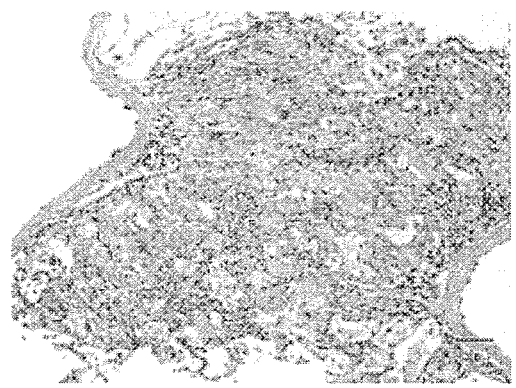
FIG. 1A is an optical photomicrograph (×200, HE-stained) showing fibrosis in lung tissues of a Japanese white rabbit, which was taken one week after administration of a fibrosis-causing agent pertaining to Example 1.
Figure 1B:
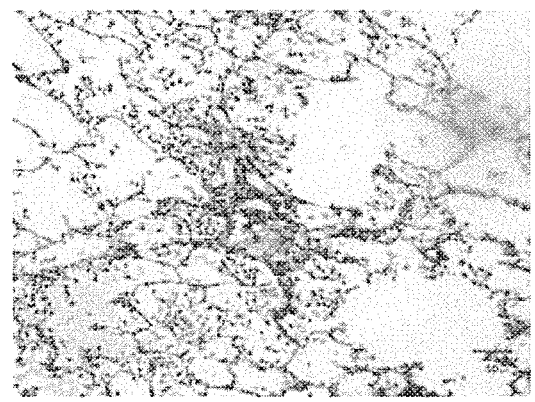
FIG. 1B is an optical photomicrograph (×200, HE-stained) showing fibrosis in lung tissues of a Japanese white rabbit, which was taken four weeks after administration of the fibrosis-causing agent pertaining to Example 1.
Figure 1C:
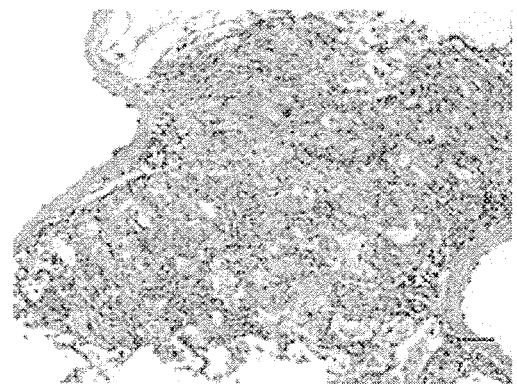
FIG. 1C is an optical photomicrograph (×200, HE-stained) showing granulomatous inflammation in lung tissues of a Japanese white rabbit, which was taken one week after administration of the fibrosis-causing agent pertaining to Example 1.
Figure 1D:
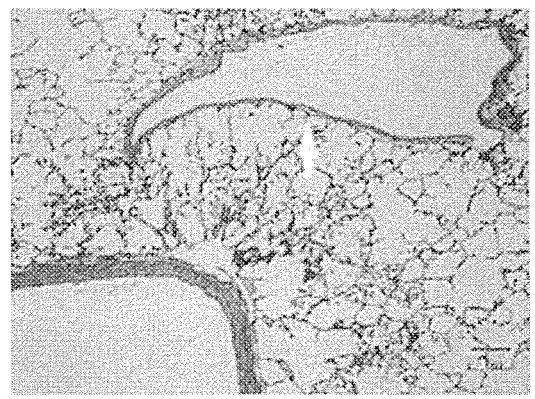
FIG. 1D is an optical photomicrograph (×100, HE-stained) showing granulomatous inflammation in lung tissues of a Japanese white rabbit, which was taken four weeks after administration of the fibrosis-causing agent pertaining to Example 1.

The following is a detailed description of an embodiment of the present disclosure.

Fibrosis-Causing Agent

One embodiment of the present disclosure provides a fibrosis-causing agent containing a fibrosis inducer and a fibrosis promoter.

Fibrosis Inducer

The fibrosis inducer is intended to induce the fibrosis of tissues. The tissues should preferably be those of trachea or lung although they are not specifically restricted. More particularly, they should preferably be those of bronchiole, respiratory bronchiole, pulmonary alveolus, and alveolar sac, with the last two being more preferable.

Examples of the foregoing fibrosis inducer include, without specific restrictions, polycation, polyanion, composite of polycation and polyanion, biodegradable material, flexible cured polymer, adhesive material, and other compounds.

The foregoing polycation is exemplified by polymers having amino groups, without specific restrictions. Typical examples of the polycation include polyamino acid, synthetic polypeptide, thrombin, polycationic polymer chitosan (such as polyvinylamine and polyallylamine), partially deacetylated chitin, and basic polysaccharide (such as aminated cellulose).

The polyamino acid or synthetic polypeptide is exemplified by polymers composed of positively charged amino acid such as lysine, arginine, histidine, ornithine, and 5-hydroxylysine. Their typical examples include poly-D-lysine, poly-L-lysine, poly-DL-lysine, polyarginine, polyhistidine, polyornithine, polyethylamine, and poly-γ-benzyl-L-glutamate. The foregoing polyamino acid or synthetic polypeptide should preferably be one which has aminoacid residues as many as 20 to 4000, preferably 50 to 3000, more preferably 100 to 1000, and most desirably 200 to 750. Moreover, the polycation should preferably be one which has a molecular weight of 10 to 500 kD, preferably 20 to 250 kD, and more preferably 30 to 200 kD. Incidentally, the foregoing polyamino acid or synthetic polypeptide may be produced by any known method, such as chemical synthesis or recombinant DNA technology. The molecular weight is one which may be determined by any known method, such as electrophoresis, size exclusion chromatography, and multi-angle laser beam scattering.

The foregoing polyanion is exemplified, without specific restrictions, by polymers having any of carboxyl group, sulfo group, and phenolic hydroxyl group. Typical examples of the polyanion include alginic acid, alginate, alginic ester, fibrin, fibrinogen, heparin, heparan sulfate, glucuronic acid, mannuronic acid, guluronic acid, dermatan sulfate, condroitin sulfate, pentosan sulfate, keratan sulfate, mucopolysaccharide polysulfate, hyaluronic acid, and polymer (such as polyglutamic acid and polyaspartic acid) composed of negatively charged amino acids (such as glutamic acid and aspartic acid).

The foregoing alginic acid is a polymer composed of β-D-mannuronic acid (M) and α-L-glucuronic acid (G). It varies in its properties depending on the molecular weight of M and G and the ratio between the amounts of M and G. For example, the one with a high G content easily forms a stable composite material (in gel form) with divalent cations such as calcium ions. The resulting gel readily crosslinks to become hard and strong. The crosslinked gel has a large number of crosslink points which help reduce the amount of water to be held therein. By contrast, the alginic acid with a high M content provides a gel which is superior in flexibility and resilience and capable of holding a large amount of water. Moreover, the alginic acid is not specifically restricted in the ratio (M/G) between the contents of β-D-mannuronic acid (M) and α-L-glucuronic acid (G). Any adequate ratio should be selected according to the intention of inducing fibrosis. This intention may be achieved by carefully selecting raw materials originating from marine algae.

The foregoing alginate includes, for example, sodium alginate, potassium alginate, calcium alginate, iron alginate, and ammonium alginate.

The foregoing alginic ester includes those esters of alginic acid with a C1 to C6 alcohol. The latter is exemplified by monohydric alcohol (such as methanol, ethanol, propanol, isopropyl alcohol, and butanol), diol (such as ethylene glycol and propylene glycol), and triol (such as glycerin). Typical examples of the alginic ester include propylene glycol alginate, methyl alginate, ethyl alginate, and ethylene glycol alginate. The preferred alginic acid is propylene glycol alginate.

The polyanion capable of forming a composite material with the polycation includes those listed below and others: heparan sulfate, heparin/heparan sulfate, dermatan sulfate, condroitin sulfate, pentosan sulfate, keratan sulfate, keratin sulfate, mucopolysaccharide polysulfate, carrageenan, sodium alginate, potassium alginate, hyaluronic acid, polyglutamic acid, polyaspartic acid, carboxymethylcellulose, randomly structured nucleic acid; polysaccharides (such as cellulose, xylose, N-acetyllactosamine, glucuronic acid, mannuronic acid, and guluronic acid), sulphated products thereof, and carboxymethylated products thereof; polyamino acid containing a plurality of amino acids selected from the group consisting of Asp, Glu, Lys, Orn, Arg, Gly, Ala, Val, Leu, Ile, Met, Pro, Phe, Trp, Asn, Gln, Ser, Thr, Tyr, Cys, and His, with Asp and/or Glu accounting for no less than about 25% of the amino acids and Lys, Orn, and Arg accounting for no more than about 5% of the amino acids; and polyamino acid represented by any of the following formulas: poly(X—Y), poly(X—Y—Y), and poly(X—Y—Y—Y), where X independently denotes Asp or Glu, and Y independently denotes Gly, Ala, Val, Leu, Ile, Met, Pro, Phe, Trp, Asn, Gln, Ser, Thr, Tyr, Cys, or His.

The biodegradable material includes any known ones, such as thrombin, borate, calcium, magnesium, chondroitin sulfate, hyaluronic acid, protein (such as gelatin), starch, collagen, glucosaminoglycan, agarose, dextran, pullulan, polyglycolic acid, polylactic acid, polyaspartic acid, polycaprolactone, polyhydroxybutyric acid, polydioxanone, "plastarch," zein, polydioxane, polylactic acid-glycolic acid copolymer, polysaccharide, soybean protein, phospho-lipid, cholesterol, phospholipid-cholesterol copolymer, polymalic acid, sacran, polyhydroxy butyrate/valerate, polycaprolactam, polybutylene succinate, polybutylene succinate/adipate, polyethylene succinate, aliphatic polyester, vinyl acetate, methyl acrylate, vinyl acetate-methyl acrylate copolymer, biomaterial (such as autologous blood), and decomposition product resulting from decrosslinking. Additional examples are biodegradable materials disclosed in Japanese Patent Laid-open Nos. 2000-160034 and 2002-146219.

The adhesive material includes, for example, talc, tetracycline, Picibanil (OK432), anticancer drug, povidone-iodine, and silver nitrate, which chemically stimulate the pleura, thereby causing pleuritis. The talc is hydrated magnesium silicate $[Mg_3Si_4O_{10}(OH)_2]$, which is composed mainly of $SiO_2$ (about 60%), MgO (about 30%), and water of crystallization (4.8%). The Picibanil (OK432) is *Streptococcus pyogenes* (Group A, Type 3) strain Su (a species of hemolytic *streptococcus*), in the form of penicillin-treated freeze-dried powder. The anticancer drug includes bleomycin, cisplatin, etc.

Desirable examples of other compounds as the fibrosis inducer mentioned above include polyvinyl alcohol, cellulose, xylose, N-acetyllactosamine, carrageenan, carboxymethylcellulose, borate, boronate, calcium, magnesium, guluronic acid, heparan sulfate, dermatan sulfate, pentosan sulfate, keratan sulfate, mucopolysaccharide polysulfate, hydrogel, acrylamide, agarose, keratin, chitin, chitosan, partially deacetylated chitin, basic polysaccharide (such as aminated cellulose), acrylamide, polyurethane, polyethylene, polyester, fluoroplastics, silica, silicone, hydroxyapatite, ceramics, bone cement, glass, metal, silicon compound, siloxane, crosslinked polymer, porous material, and such material as disclosed in Japanese Patent Laid-open No. 2001-164127.

The above-mentioned compounds as the fibrosis inducer may be used alone or in combination with one another.

The fibrosis inducer mentioned above should preferably contain a polyanion selected from the group consisting of alginic acid, alginate, and alginic ester.

The fibrosis inducer may be in the form of liquid, gel, or solid (particles).

In the case where the fibrosis inducer is in the form of particulate solid, the particles should preferably have an average particle diameter no larger than twice (more preferably one time) the entrance diameter of enlarged pulmonary alveolus or alveolar sac. The average diameter specified above is necessary for the particles to be retained in the pulmonary alveolus or alveolar sac. Incidentally, the entrance diameter of the enlarged pulmonary alveolus or alveolar sac varies depending on the patient's weight and the degree of seriousness and the position of pulmonary emphysema. It is usually 1 to 2 mm in the case of human patient.

Moreover, the fibrosis inducer should preferably have an average particle diameter larger than (more preferably no smaller than 1.1 times) the entrance diameter of the normal pulmonary alveolus or alveolar sac. The average diameter specified above is necessary for the fibrosis inducer to be excluded from normal pulmonary alveoli or alveolar sacs but to enter enlarged pulmonary alveoli or alveolar sacs, thereby causing fibrosis there only. Incidentally, the entrance diameter of normal pulmonary alveolus or alveolar sac varies depending on the patient's weight and other factors. It is usually 200 to 300 μm in the case of healthy human.

The average particle diameter of the fibrosis inducer should be 200 nm to 2000 μm, preferably 1 μm to 1000 μm. An average particle diameter no smaller than 200 nm is necessary for the fibrosis inducer to be protected from phagocytosis by macrophage or dendritic cell. By contrast, an average particle diameter no larger than 2000 μm is desirable for the fibrosis inducer to have a large surface area for sufficient contact with tissues. Incidentally, the value of "average particle diameter" used in this specification is measured by observation under a scanning electron microscope (SEM) or transmission electron microscope (TEM). It is calculated by averaging particle diameters of particles observed in several to dozens of visual fields. The term "particle diameter of particle" means the maximum distance between any two points on the particle contour at which the particle contour crosses the line passing through the particle center.

In the case where the fibrosis-causing agent is in the form of solid, the fibrosis inducer mentioned above may have surface treatment produced by exposure to plasma, addition of polyethylene glycol, cationization, or anionization. The surface treatment improves the fibrosis-causing agent in adhesive property and fibrosis-causing performance and also in protection against phagocytosis by macrophage or dendric cell.

Fibrosis Promoter

The fibrosis promoter is intended to promote the fibrosis of tissues induced by the fibrosis inducer mentioned above. Usually, it does not bring about the fibrosis of tissues by itself.

Examples of the fibrosis promoter include the following without specific restrictions: platelets, erythrocytes, leukocytes, serum, plasma, platelet-rich plasma (PRP), autologous blood, marrow fluid, marrow-originating cells, mesenchymal stem cells, fat, fat stem cells, and other components (such as stem cells) derived from living bodies; and fibroblast growth factor (FGF), platelet-derived growth factor (PDGF), vascular endothelial growth factor (VEGF), nerve growth factor (NGF), epidermal growth factor (EGF), insulin-like growth factor (IGF), transforming growth factor (TGF), brain-derived neurotrophic factor (BDNF), granulocyte colony stimulating factor (G-CSF), granulocyte macrophage colony stimulating factor (GM-CSF), erythropoietin (EPO), thrombopoietin (TPO), basic fibroblast growth factor (bFGF or FGF2), hepatocyte growth factor (HGF), bone morphogenetic protein (BMP), neurotrophin (neurotrophic factor: NGF, BDNF, NT3, etc.), and other growth factors belonging to the family of the above-mentioned factors.

Preferable among the foregoing examples of fibrosis promoter are platelets and PRP, with the latter being most desirable. They may be used alone or in combination with one another.

The foregoing PRP contains platelets and plasma, and may also contain blood components and anticoagulant.

The plasma contains water, albumin, protein (such as immunoglobulin), lipid, carbohydrate, and inorganic salts (such as sodium ions, potassium ions, and phosphate ions).

The blood components include leukocytes and erythrocytes.

The anticoagulant includes sodium citrate, ethylenediaminetetraacetic acid (EDTA), acid citrate dextrose solution (ACD), and sodium fluoride, which serve as a calcium chelating agent.

Additional examples of the anticoagulant include vitamin K dependent blood coagulation factor synthetic inhibitor (such as warfarin, acenocoumarol, and phenindione); thrombin inhibitor (such as dabigatran and argatroban); factor Xa inhibitor (such as rivaroxaban, edoxaban, apixaban, and fondaparinux); and heparin and low-molecular weight heparin. Preferable among these examples is calcium chelating agent, particularly sodium citrate. Incidentally, the foregoing anticoagulants may be used alone or in combination with one another.

Platelets and PRP can be obtained usually by centrifuging blood or with the help of a PRP producing unit (such as Smart PreP2 made by Harvest Technologies Corp. of Terumo group). The ordinary process for preparation of PRP consists of adding an anticoagulant to collected blood for prevention of blood coagulation, and centrifuging the treated blood. The centrifugation separates the blood into blood cell component containing erythrocytes, buffy coat containing platelets and leukocytes, and supernatant containing plasma. The thus obtained supernatant is platelet-rich plasma (PRP). Incidentally, the resulting PRP may be centrifuged again to remove erythrocytes remaining in the supernatant. In other words, the repeated centrifugation of PRP gives rise to more purified buffy coat and nearly platelet-free plasma or platelet-poor Plasma (PPP), which are mixed together again to yield purified PRP.

The fibrosis inducer and the fibrosis promoter should preferably be mixed together in a ratio of from 1:0.2 to 1:10 (by mass), more preferably from 1:0.5 to 1:5 (by mass).

In the case where the fibrosis promoter is platelets or PRP, the ratio of the fibrosis inducer to the platelets (if the fibrosis promoter is PRP, platelets contained therein) should preferably be from 1:0.2 to 1:10 (by mass), more preferably from 1:0.5 to 1:5 (by mass).

In the case where the fibrosis promoter is PRP, the content of platelets in PRP should preferably be 5×104 to 1000×104 cells/pt, more preferably 10×104 to 500×104 cells/pt. Incidentally, the content of platelets in PRP may be determined by measurement with a multi-item automatic hemocyte counter.

In the case where the fibrosis promoter is PRP, the content of anticoagulant should preferably be 0.01 to 20 mg/mL, more preferably 0.01 to 10 mg/mL, in 1 mL of blood, depending of the type of anticoagulant.

The fibrosis-causing agent pertaining to this embodiment is superior to conventional ones in its fibrosis performance because, as mentioned above, it is composed of the fibrosis inducer (which induces fibrosis) and the fibrosis promoter (which promotes fibrosis) similar to various growth factors released from platelets. This efficient fibrosis is attributable to the synergistic action of the fibrosis inducer and the fibrosis promoter.

According to one embodiment of the present disclosure, the combination of the fibrosis inducer and the fibrosis promoter is such that any one of alginic acid, alginate, and alginic ester is combined with any one of platelets and PRP. A desirable combination is alginate and PRP. A more desirable combination is any one of sodium alginate, calcium alginate, and iron alginate and PRP. The most desirable combination is calcium alginate and PRP. This combination is effective for the above-mentioned synergistic effect.

Adjuvants

The fibrosis-causing agent may be incorporated, without specific restrictions, with a variety of adjuvants selected according to the type and seriousness of the disease to which it is applied.

Examples of the adjuvants include platelet-rich plasma (PRP) gelling agent, solvent, antibiotic, and steroid. Additional adjuvants include lipid and surface active agent, which make the fibrosis inducer stable and multifunctional.

Platelet-Rich Plasma (PRP) Gelling Agent

The platelet-rich plasma (PRP) gelling agent causes PRP to gel. Consequently, it is used in the case where the fibrosis promoter is PRP. Gelation permits the fibrosis-causing agent to stay firm at the affected part. This means that the fibrosis-causing agent even in a small amount can bring about fibrosis.

A preferred example of the platelet-rich plasma (PRP) gelling agent may contain at least one selected from calcium, calcium salt, fibrin, fibrinogen, thrombin, vitamin K, and blood coagulation factor X ("factor X").

The calcium salt mentioned above includes, for example, calcium chloride, calcium sulfate, calcium nitrate, calcium formate, calcium citrate, calcium malate, calcium tartrate, calcium gluconate, calcium succinate, calcium malonate, calcium glutarate, calcium maleate, calcium fumarate, calcium glutaconate, and calcium lactate.

The PRP gelling agent as exemplified above may be used alone or in combination with one another.

An adequate selection of the PRP gelling agent depends on the anticoagulant used at the time of preparation of PRP. For example, in the case where the anticoagulant used to prepare PRP is the calcium chelating agent mentioned above, the desirable PRP gelling agent is calcium or calcium salt. Moreover, in the case where preparation of PRP employs any of vitamin K dependent blood coagulation factor synthetic inhibitor, thrombin inhibitor, factor Xa inhibitor, and heparin and low-molecular weight heparin, the preferable PRP gelling agent is any of vitamin K, thrombin, factor X, fibrin, and fibrinogen.

Incidentally, calcium, fibrin, fibrinogen, and thrombin function also as the fibrosis inducer. Therefore, in the case where the anticoagulant used at the time of preparation of PRP is any of calcium chelating agent, thrombin inhibitor, and heparin and low-molecular weight heparin, any of calcium, fibrin, fibrinogen, and thrombin used as the PRP gelling agent functions also as the fibrosis inducer and PRP gelling agent.

Calcium salt, among the numerous PRP gelling agents, may be used as an adequate adjuvant in the case where the fibrosis inducer is any of alginic acid, alginate, and alginic ester, even though PRP is not used as the fibrosis promoter. Alginic acid readily reacts with calcium salt to form a stable composite material and thus turns into gel, as mentioned above. Consequently, if the fibrosis-causing agent is to be administered in the dosage form of gel, it is possible to add a calcium salt as the gelling agent for alginic acid. In other words, the calcium salt functions as the gelling agent for alginic acid and derivatives thereof.

The fibrosis promoter and the PRP gelling agent should be used in a ratio from 1:0.001 to 1:10 (by mass), preferably from 1:0.003 to 1:5 (by mass).

Particularly in the case where the fibrosis promoter is PRP and the PRP contains an anticoagulant, the ratio of the anticoagulant to the PRP gelling agent should be from 1:0.001 to 1:5 (by mass), preferably 1:0.002 to 1:1 (by mass).

In the case where the fibrosis inducer is alginic acid or a derivative thereof and the PRP gelling agent is added for gelation of alginic acid or derivative thereof, the ratio of the alginic acid (or a derivative thereof) to the PRP gelling agent should be from 1:0.001 to 1:10 (by mass), preferably from 1:0.003 to 1:5 (by mass).

(Solvent)

The fibrosis-causing agent may be incorporated with a solvent as an adjuvant so that it is made fluid. This holds true in the case where the fibrosis-causing agent lacks fluidity.

The solvent is not specifically restricted so long as it has no adverse effects on living bodies. It includes, for example, water, physiological saline, Ringer's solution, dimethylsulfoxide (DMSO), dimethylformamide (DMF), HCl, alcohol, glycerol, and any other aqueous solution (containing water as solvent). These solvents may be used alone or in combination with one another.

The fibrosis-causing agent may contain solvents in varied amounts depending on its dosage form, ranging from approximately 5 to approximately 300% (by mass), preferably approximately 10 to approximately 200% (by mass), of its mass.

Antibiotics

An antibiotic may be added to prevent acute exacerbation due to infection.

Examples of the antibiotics include, without specific restrictions, β-lactam antibiotics (such as penicillin, cephem, oxacephem, penem, carbapenem, and monobactam); aminoglycoside antibiotics; tetracycline antibiotics; chloramphenicol; lincomycin-streptogramine antibiotics; polypeptide antibiotics; polyene antibiotics; flucytosine; azole antifungal drugs; terbinafine, butenafine, and amorolfine; and antiviral agents.

The foregoing β-lactam antibiotics include, for example, benzylpenicillin, methicillin, cloxacillin, ampicillin, amoxicillin, bacampicillin, carbenicillin, sulbenicillin, cephaloridine, cefotiam, cefoperazone, cefmetazole, latamoxef, flomoxef, imipenem, panipenem, imipenem-cilastatin mixture, panipenem-betamipron mixture, aztreonam, and faropenem sodium.

The foregoing aminoglycoside antibiotics include, for example, streptomycin, kanamycin, gentamicin, sisomicin, dibekacin, amikacin, tobramycin, arbekacin, and isepamicin.

The foregoing tetracycline antibiotics include, for example, tetracycline, oxytetracycline, minocycline, and demethylchlortetracycline.

The foregoing lincomycin-streptogramine antibiotics include, for example, lincomycin, clindamycin, and quinupristin-dalfopristin mixture.

The foregoing polypeptide antibiotics include, for example, colistin, polymixin B, vancomycin, and teicoplanin.

The foregoing polyene antibiotics include, for example, amphotericin B, nystatin, trichomycin, and flucytosine.

The foregoing azole antifungal drugs include, for example, econazole, miconazole, fluconazole, and itraconazole.

The foregoing antiviral agent includes, for example, aciclovir, vidarabine, ganciclovir, amantadine, rimantadine, zanamivir, oseltamivir, zidovudine, didanosine, lamivudine, indinavir ethanolate, ritonavir, saquinavir, interferon preparations, and ribavirin.

The antibiotics listed above may be used alone or in combination with one another.

The fibrosis-causing agent may contain any of the foregoing antibiotics in an amount of approximately 0.0005 to approximately 1% (by mass) based on its mass.

The antibiotics may be administered in a dose of approximately 5 to approximately 1000 µg/mL.

Additional Adjuvants

The fibrosis-causing agent may also contain any of additional adjuvants listed below:

radiopaque materials (such as metrizamide, iopamidol, sodium iothalamate, iodamide sodium, and meglumine, which are water-soluble, and gold, titanium, silver, stainless steel, aluminum oxide, and zirconium oxide, which are water-insoluble); contrast enhancer (such as paramagnetic material, heavy atoms, transition metal, lanthanide, actinide, dye, and radioactive nuclear species); steroid; bronchodilator; lipid (such as acylglycerol, neutral fat, wax, ceramide, phospholipid, sphingophospholipid, glycerophospholipid, glycolipid, sphingoglycolipid, glyceroglycolipid, lipoprotein, sulfolipid, isoprenoid, fatty acid, terpenoid, steroid, and carotenoid); anionic surface active agent (such as sodium salt of fatty acid, monoalkyl sulfate, alkylpolyoxyethylene sulfate, alkylbenzene sulfonate, and monoalkyl phosphate); cationic surface active agent (such as alkyltrimethyl ammonium salt, dialkyldimethyl ammonium salt, and alkylbenzyldimethyl ammonium salt); amphoteric surface active agent (such as alkyldimethylamineoxide and alkylcarboxybetaine); and nonionic surface active agent (such as polyoxyethylene alkyl ether, fatty acid sorbitan ester, alkyl polyglycoside, fatty acid diethanolamide, and alkyl monoglyceryl ether.

The additional adjuvants mentioned above may be used alone or in combination with one another.

The amount of the additional adjuvants may vary, without specific restriction, depending on the type and seriousness of the disease to which the fibrosis-causing agent is applied. The content of the additional adjuvants is 1 to 200% (by weight) with respect to the fibrosis-causing agent.

Dosage Form

The fibrosis-causing agent may be administered in any form (such as liquid, gel, particles, and capsules) without specific restrictions.

It is only necessary for the fibrosis-causing agent to assume the desired dosage form at the target part. Consequently, it is possible to administer the fibrosis inducer and the fibrosis promoter (as the constituents of the fibrosis-causing agent) separately in such a way that they produce the desired dosage form at the target part.

In addition, the fibrosis-causing agent may be composed of the fibrosis inducer and the fibrosis promoter which are different in property. For instance, the former may be a solid and the latter may be a gel. In this case, the former may be dispersed in the latter. Alternatively, the fibrosis-causing agent may be in the form particles or capsules, and in this case the fibrosis inducer may be contained in the fibrosis-causing agent.

The fibrosis-causing agent may assume any dosage form which varies depending on the type of administration to be determined according to the state of the patient or affected part. For instance, the fibrosis-causing agent should preferably be in the dosage form of liquid or particles for administration to a patient whose bronchial epitheliocytes are poor in resilience due to aging. Also, the fibrosis-causing agent should preferably be in the dosage form of viscous liquid, gel, or particles for administration to a patient who has severe emphysema, in which case the fibrosis-causing agent securely stays in the affected part.

Administration of the fibrosis-causing agent in the dosage form of gel may present difficulties in its delivery to the target part on account of its high viscosity. This problem may be addressed by employing a catheter which permits the fibrosis-causing agent to be delivered efficiently under pressure or administered immediately after gelation. Another possible way is to administer the fibrosis inducer and the fibrosis promoter separately and then administer the PRP gelling agent so that gelation takes place at the affected part. Incidentally, the fibrosis-causing agent varies in time required for gelation. An adequate length of time can be attained by adjusting the structure of alginic acid (e.g., M/G ratio and molecular weight), the amount and concentration of the PRP gelling agent, and the concentration of the anticoagulant.

In the case where the fibrosis-causing agent is not administered in its completed form but in the form of combination of its separate components which turn into the fibrosis-causing agent at the affected part, it is desirable to use the individual components (i.e., fibrosis inducer, fibrosis promoter, optional PRP gelling agent, solvent, and antibiotics) as a kit.

Use Applications

The fibrosis-causing agent according to the embodiment of the present disclosure is capable of causing fibrosis of tissues as desired. It may be applied to any part without specific restrictions. Among those parts to which it is properly applied are trachea and lung tissues, more preferably bronchioles, respiratory bronchioles, pulmonary alveoli, and alveolar sacs, with the last two being most desirable. The fibrosis-causing agent brings about fibrosis in the lung tissues of a patient suffering from pulmonary emphysema, thereby reducing the lung capacity.

Thus, the fibrosis-causing agent according to one embodiment of the present disclosure can be properly applied to the lung for treatment of pulmonary emphysema.

The dose of the fibrosis-causing agent to be administered for treatment of pulmonary emphysema varies depending on the state of patient. It is usually 0.1 to 50 mL/kg, preferably 0.3 to 10 mL/kg.

Method for Fibrosis

The fibrosis-causing agent according to one embodiment of the present disclosure may be applied in various methods as mentioned below.

The first method for fibrosis consists of inserting a catheter into the trachea, bronchus or bronchiole through the respiratory tract (step (a)) and delivering the fibrosis-causing agent to the respiration region (including pulmonary alveoli or alveolar sacs) through the catheter (step (b)).

The second method for fibrosis consists of inserting a rigid endoscope and a needle tube (for administration) in the thoracic cavity (step (c)) and administering the fibrosis-causing agent below the pleura through the needle tube (step (d)).

The third method for fibrosis consists of opening the chest (step (e)) and administering the fibrosis-causing agent to the desired part (step (f)).

Fibrosis should preferably be performed on pulmonary alveoli or alveolar sacs. In addition, fibrosis should preferably be performed for treatment of pulmonary emphysema.

The term "respiratory region" used in this specification generically denotes the respiratory organ beyond the bronchus, including respiratory bronchioles and two alveoli. To be concrete, the respiratory region includes bronchi, bronchioles, terminal bronchioles, respiratory bronchioles, alveolar ducts, pulmonary alveoli, alveolar sacs, pulmonary veins, and pulmonary arteries. It should preferably include alveolar ducts, pulmonary alveoli, alveolar sacs, pulmonary veins. In this specification, the term "pulmonary alveoli or alveolar sacs" denotes at least either of pulmonary alveoli or alveolar sacs, and they are collectively called "alveolar parenchyma."

The fibrosis-causing agent may be administered to any object, particularly mammals, without specific restrictions. Typical examples of mammals include human, pet, household animal, and farm animal (such as rabbit, dog, cat, horse, sheep, goat, primate, cow, pig, rat, and mouse). Preferable among them are human, rabbit, dog, and pig, with human being most desirable.

The following is a detailed description of the first method mentioned above.

Step (a)

This step involves insertion of a catheter into the trachea, bronchus, or bronchiole through the respiratory tract. The catheter may be inserted into any position, however, it should preferably be inserted such that its forward end extends as far as the eighth branch or beyond it. The reason for this is that the opening of enlarged pulmonary alveolus usually exists beyond the eighth to twelfth branches. The catheter inserted in this manner permits (in step (b) that follows) the fibrosis-causing agent to be delivered in a maximum amount selectively to a narrow affected part, i.e., the enlarged pulmonary alveolus or alveolar sac (which are simply referred to as "enlarged alveolar parenchyma" hereinafter). As a result, the thus administered fibrosis-causing agent effectively induces fibrosis. In addition, insertion of the catheter up to or beyond the eighth branch prevents the fibrosis-causing agent from entering the normal pulmonary alveoli or alveolar sacs (which are simply referred to as "normal alveolar parenchyma" hereinafter). This is an effective way of preventing normal pulmonary alveoli or alveolar sacs from fibrosis while keeping them intact. In view of the foregoing, the catheter for treatment of a human patient should preferably be one which has a diameter of 1.5 to 5 mm, more preferably 2 to 4 mm. Incidentally, the first right-left branch of the trachea is defined as the first branch in this specification.

The catheter is not specifically restricted; it may be properly selected according to the diameter (or the number of branches) of the bronchus or bronchiole into which it is inserted. To be concrete, acceptable catheters include any known medical ones for the respiratory organ, circulatory organ, and digestive organ. The catheter may be used according to the method disclosed in U.S. Patent Application Publication No. 2006/0283462. Moreover, the catheter is not specifically restricted in its structure; it may or may not have a balloon. The one having a balloon is preferable from the standpoint of easy delivery and administration of the fibrosis-causing agent into the trachea. The catheter is not restricted either in the number of lumens and the inside diameter. Adequate values for them should be selected according to the fibrosis-causing agent to be administered (which varies in dose, property, shape, and adjuvants) and the presence or absence of a balloon.

Insertion of a catheter into the vicinity of an enlarged alveolar parenchyma may be accomplished with the help of a sheath inserted into a part close to the enlarged alveolar parenchyma. The sheath is not specifically restricted in structure, it may or may not have a balloon. However, it should preferably have a balloon which closes the bronchus or bronchiole. The balloon fixes the sheath to the bronchus or bronchiole, thereby allowing the catheter to be stably inserted into the desired position. The balloon attached to the sheath and the balloon attached to the catheter may be placed at any position in the bronchus or bronchiole without specific restrictions. It is desirable that the balloon attached to the sheath be placed at the bronchus and the balloon attached to the catheter be placed at the bronchus near the terminal, particularly at the bronchiole. Closing the bronchus or bronchiole with a balloon as mentioned above increases airtightness in the region beyond the sheath, thereby allowing the fibrosis-causing agent to be introduced and administered efficiently into the enlarged alveolar parenchyma through the catheter. It is possible to cause two balloons attached to the sheath and catheter respectively to close different parts in the bronchus or bronchiole, so as to easily control the pressure on the normal alveolar parenchyma (existing between the two balloons) or the pressure on the enlarged alveolar parenchyma) beyond the balloon of the catheter.

Closing the bronchus or bronchiole with the balloon of the sheath ensures ventilation with respiration pressure in the near side from the balloon of the sheath. This leads to efficient and safe treatment. The balloon of the sheath may be inflated and deflated in any way without specific restrictions, for example, by means of a three-way stopcock attached to the base of the sheath.

It is possible to stably manipulate the fore-end of the catheter if the pressure is kept constant in the region beyond the balloon attached to the sheath. This is accomplished, for example, by closing the bronchus or bronchiole with the balloon of the sheath and decompressing the region beyond the sheath. This procedure permits the balloon of the catheter to closely adhere to the wall of the bronchus or bronchiole and also prevents air from entering the region beyond the catheter through the side passage. The result is easy decompression in the region beyond the catheter. The reduced pressure (lower than the injection pressure of the fibrosis-causing agent) in the region beyond the sheath facilitates the introduction and administration of the fibrosis-causing agent at a constant pressure into the region beyond the catheter. No specific restrictions are imposed on the method of controlling the pressure at the fore-end of the sheath or the fore-end of the catheter. To be specific, the pressure control may be accomplished by inserting the catheter into the sheath through a sealing valve attached to the proximal end of the sheath. The sealing valve closes the alveolar parenchyma beyond the fore-end of the sheath. This permits easy pressure control at that part. It is also possible to control pressure in the alveolar parenchyma beyond the fore-end of the sheath, if the proximal end of the sheath is provided with a three-way stopcock through which air is introduced and discharged. The foregoing method may be applied also to the pressure control beyond the fore-end of the catheter. The sealing valve attached to the base of the catheter closes the alveolar parenchyma beyond the fore-end of the catheter. This permits easy pressure control at that part. It is also possible to control pressure in the alveolar parenchyma beyond the fore-end of the catheter, if the proximal end of the catheter is provided with a three-way stopcock through which air is introduced and discharged. Moreover, the inflation and deflation of the catheter's balloon may be accomplished in any way, without specific restrictions, by means of the three-way stopcock attached to the proximal end of the catheter. In addition, the catheter may have a lumen for a guide wire which facilitates the insertion of the catheter to the desired position.

The catheter suitable for the foregoing method is one which is provided with a balloon to close the bronchus and also with a lumen which has openings at a far part and a near part and delivers a liquid to the far part. Another example of the catheter is a percutaneous transluminal coronary angioplasty (PTCA) catheter of over-the-wire (OTW) type which is designed for treatment of cardiovascular stenosis. These catheters may be any commercial ones listed below. Microcatheter (FINECROSS® (made by Terumo Corp.) that permits passage of a guide wire to cardiovascular stenosis. PTCA catheter (Ryujin Plus OTW®, made by Terumo Corp.). Occlusion microballoon catheter (ATTENDANT®, made by Terumo Clinical Supply Co., Ltd.). The foregoing catheter is inserted into the bronchus through the working lumen of a bronchoscope. Using a bronchoscope is not essential if the catheter is arranged at any desired position. The catheter and the catheter's balloon (in its inflated state) are not specifically restricted in diameter; an adequate diameter should be selected according to the diameter of the bronchus and bronchiole. To be concrete, the outside diameter of the inflated balloon of the catheter should preferably be slightly larger than the inside diameter of the bronchus or bronchiole in which the fore-end of the inserted catheter lies. To be more specific, the outside diameter (Y mm) of the inflated balloon should be about one to two times larger than the inside diameter (X mm) of the bronchus or bronchiole. This ratio is suitable for the catheter or balloon to come into close contact with the bronchus or bronchiole (which is formed from elastic smooth muscles) without severe damage.

This step (a) may be carried out in such a way that, prior to insertion of the catheter into the bronchus or bronchiole, a guide wire is inserted into the catheter's lumen (for fluid delivery). Manipulation in this way permits the fore-end of the guide wire to be placed beyond the fore-end of the catheter or near the peripheral position. Thus, the fore-end of the catheter can be introduced to the vicinity of pulmonary alveoli or alveolar sacs (air sacs) beyond the bronchus or bronchiole. The guide wire to be used for this purpose may be any known one designed for pulmonology, cardiology, and gastroenterology. It should have an adequate outside diameter which depends on the size of the lumen of the catheter to be used. Its typical example is Runthrough® for cardiology (made by Terumo Corporation), having an outside diameter of 0.014 inch.

It is desirable that the fore-end of the guide wire and catheter be provided with a member (agent) capable of radiographic imaging. This arrangement permits the operator to confirm the position of the fore-end of the guide wire and catheter (which projects from the fore-end of the endoscope) at the time of observation by X-ray radioscopy. In this way the operator can introduce the guide wire and catheter to the respiratory region (including enlarged pulmonary alveoli or alveolar sacs) which have previously been identified by X-ray radioscopy or computed tomography (CT) scan. In this occasion, the guide wire is pulled away after it is confirmed by X-ray radioscopy that the fore-end of the catheter has reached the desired position. The foregoing operation should preferably be performed in such a way that the fore-end of the guide wire is placed beyond the fore-end of the catheter. Moreover, the fore-end of the catheter should preferably have a network structure or perforated structure so that it will not adhere to the inner wall of the respiratory region (such as pulmonary alveoli and alveolar sacs).

Step (b)

This step is intended to administer the fibrosis-causing agent to the respiratory region (including pulmonary alveoli and alveolar sacs) through the catheter which has been inserted by the step (a) mentioned above. The operation by this step effectively places the fibrosis-causing agent in the affected part (enlarged alveolar parenchyma), thereby inducing and promoting fibrosis in the affected part and hence reducing the lung capacity.

Administration in this step may be performed in any manner, without specific restrictions, because the fibrosis-causing agent takes on various dosage forms as mentioned above. One method involves preparation of the fibrosis-causing agent and subsequent administration of the fibrosis-causing agent. Another method involves administration of the fibrosis inducer and fibrosis promoter and subsequent administration of the PRP gelling agent. Still another method involves administration of the fibrosis promoter and subsequent sequential administration of the fibrosis inducer and the PRP gelling agent. The fibrosis inducer, the fibrosis promoter, and the PRP gelling agent may be administered together with or separately from the optional solvents and antibiotics.

One preferable method involves administration of the fibrosis inducer and fibrosis promoter and subsequent administration of the gelling agent for platelet-rich plasma (PRP). Another preferable method involves simultaneous administration of the fibrosis inducer, fibrosis promoter, and PRP gelling agent mixed together.

The term "administration of the fibrosis-causing agent" used in this step implies administrating individually the constituents of the fibrosis-causing agent, because it is only necessary to create a state in which the fibrosis-causing agent is administered to the affected part.

Smooth delivery of the fibrosis-causing agent at the time of its administration will be ensured if the respiratory region is pressurized by means of a catheter.

The specific method for administration of the fibrosis-causing agent should be established according to the known technology in comprehensive consideration of the dosage form and composition of the fibrosis-causing agent to be used and the state of the patient and effected part.

For administration of the fibrosis-causing agent in particulate form, it is desirable to determine the average particle diameter of the fibrosis-causing agent based on the previously measured entrance diameter of the enlarged and/or normal pulmonary alveolus or alveolar sac. In other words, the step (b) of the procedure according to the present disclosure should be preceded by a preliminary step to measure the entrance diameter of the enlarged and/or normal pulmonary alveolus or alveolar sac and then determine the average particle diameter of the fibrosis-causing agent based on the thus measured entrance diameter. This preliminary step helps prevent the fibrosis-causing agent from discharging from enlarged pulmonary alveoli or alveolar sacs and also prevent the fibrosis-causing agent from entering normal pulmonary alveoli or alveolar sacs. Incidentally, it is possible to perform continuously or intermittently the preliminary steps to "measure the entrance diameter of the enlarged and/or normal pulmonary alveolus or alveolar sac" and "determine the average particle diameter of the fibrosis-causing agent based on the thus measured entrance diameter."

There are no specific restrictions on the method of measuring the entrance diameter of the enlarged and/or normal pulmonary alveolus or alveolar sac. The measurement may be accomplished by observation by means of endoscope or CT scan (in the case where the entrance diameter is as large as 1 mm and above). An alternative method for measurement is by X-ray radiography which is preceded by administration of a contrast agent to the bronchus. Another method involves insertion of a probe into the vicinity of the entrance of the pulmonary alveolus or alveolar sac and their imaging with ultrasound or infrared rays. If such measurements are difficult to carry out, it is possible to adopt, in place of measured values, statistical values for the entrance diameter of the enlarged and/or normal pulmonary alveolus or alveolar sac.

The fibrosis-causing agent according to this embodiment effectively induces the fibrosis of tissues; therefore, upon administration to the respiratory region by the step (b) mentioned above, it brings about fibrosis in the tissue (specifically enlarged alveolar parenchyma), thereby reducing the lung capacity. This produces the effect of relieving and preventing the lung's overexpansion that weakens the patient due to pulmonary emphysema and bronchus occlusion. The result is that the enlarged alveolar parenchyma is made smaller than its original size, and this in turn produces the effect of relieving and preventing the compression and occlusion of the bronchus by the surrounding alveolar parenchyma. In addition, the foregoing method for fibrosis relies on a catheter and needs no surgical treatment, which leads to a reduced burden on the patient. Moreover, fibrosis by the foregoing method grows the connective tissue (particularly fibroblast) on the inner wall of the enlarged alveolar parenchyma, thereby recovering the resilience of the alveolar parenchyma and relieving and preventing the lung's overexpansion.

EXAMPLES

The present disclosure will be described in more detail with reference to the following examples, which are not intended to restrict the scope thereof.

Example 1

Experiments for fibrosis were carried out in which the fibrosis inducer is sodium alginate and the fibrosis promoter is platelet-rich plasma (PRP).

(Preparation of Aqueous Solution of Sodium Alginate)

An aqueous solution (0.5% w/v) of sodium alginate was prepared by dissolving 0.15 g of sodium alginate (made by Wako Pure Chemical Industries, Ltd.) in 30 mL of reverse osmosis water (RO water), followed by filtration and sterilization through a sterilizing filter (Millipore 0.22 µm). The resulting solution was a viscous fluid.

Preparation of Platelet-Rich Plasma (PRP)

In the first step, 10 mL each of blood was collected into two syringes (10 mL) containing 1.0 mL of anticoagulant ACD-A solution (citric acid glucose solution, made by Terumo Corp.) from the auricular artery of unanesthetized Japanese white rabbits (clean, male, 3.0 to 3.49 kg). The collected blood was transferred to a 15-mL centrifuge tube, which was slowly tumbled for mixing.

The blood was centrifuged for ten minutes at 20° C. and 230×g by means of a refrigerated centrifuge (made by Kubota Corp.) for separation of the supernatant (plasma). The separated supernatant (plasma) was centrifuged for eight minutes at 20° C. and 840×g for precipitation.

The remaining blood was centrifuged for ten minutes at 20° C. and 1280×g for separation of the supernatant (platelet-poor plasma (PPP)).

The precipitates obtained as mentioned above were dispersed again in 1 mL of the platelet-poor plasma (PPP) separated as mentioned above. Thus, there was obtained the intended platelet-rich plasma (PRP).

The resulting PRP was found, by measurement with a multi-item automatic hemocyte counter (made by Sysmex Corp.), to contain platelets of $100 \times 10^4$ to $130 \times 10^4$ cells/µL. The thus obtained PRP was an ordinary liquid.

(Preparation of Fibrosis-Causing Agent)

The fibrosis-causing agent was prepared by mixing the aqueous solution of sodium alginate and the platelet-rich plasma (PRP) in a ratio of 1:1 (by volume). The resulting fibrosis-causing agent was a viscous liquid.

Administration to Animal

The test animals were Japanese white rabbits (clean, male, 3.0 to 4.49 kg).

The test animal was given (by intramuscular injection) xylazine hydrochloride (diluted four times with physiological saline) at a dose of 5 mg/kg (1 mL/kg) for preanesthetic medication.

The test animal was further given (by intravenous injection through its auricular vein) somnopentyl (sodium pentobarbiturate, diluted 3.24 times with physiological saline) at a dose of 20 mg/kg (1 mL/kg) as an anesthetic agent. The test animal which showed reflex during operation was given additional injection at a dose of 10 mg/kg (0.5 mL/kg) so that it kept the desired anesthetic depth.

After anesthetization, the test animal was given the fibrosis-causing agent at its bronchus through a catheter.

To be concrete, this procedure was carried out as follows. With its sufficient anesthetic depth confirmed, the test animal had its cervical part dissected at the median part thereof, so that the trachea was exposed. In the subsequent step, a 0.035-inch guide wire (made by Terumo Corp.) was inserted into the posterior lobe of the right lung through the dissected trachea, until the fore-end of the guide wire reached the position of the seventh rib (or the upper part of the third branch). The guide wire was passed through the lumen of a 6-Fr guiding catheter (made by Terumo Corp.) coated with lidocaine. The catheter was inserted so that the fore-end thereof reached the seventh rib, and the guide wire was pulled out.

By way of the catheter, the fibrosis-causing agent prepared as mentioned above was infused twice (0.5 mL each), air (10 mL) was infused, and the fibrosis-causing agent was infused twice again (0.5 mL each), and finally air (10 mL) was infused. Incidentally, the infusion of the fibrosis-causing agent and air was coincident with inspiration.

After administration of the fibrosis-causing agent, the test animal had its trachea sutured and then was given viccillin parenteral solution (0.5 g of ampicillin sodium diluted with 10 mL of physiological saline) at a dose of 2 mL (100 mg/head) by intramuscular injection at the paradissected part.

Example 2

Experiments for fibrosis were carried out in which the fibrosis inducer is sodium alginate and the fibrosis promoter is platelet-rich plasma (PRP). These components were used in combination with calcium chloride as the PRP gelling agent.

Preparation of Aqueous Solution of Sodium Alginate and Preparation of Platelet-Rich Plasma (PRP)

The same procedure as in Example 1 was repeated to prepare the aqueous solution of sodium alginate and the platelet-rich plasma (PRP).

Preparation of Mixed Solution

A mixed solution was prepared from the aqueous solution of sodium alginate and the platelet-rich plasma (PRP) which were mixed together in a ratio of 1:1 (by volume). The resulting mixed solution was a viscous liquid.

Preparation of Aqueous Solution of Calcium Chloride

An aqueous solution (40 mM) of calcium chloride was prepared by dissolving 0.222 g of calcium chloride (made by Wako Pure Chemical Industries, Ltd.) in reverse osmosis water (RO water) such that the resulting solution fills a 50-mL volumetric flask. This aqueous solution was autoclaved at 121° C. for 20 minutes for sterilization. The thus obtained aqueous solution of calcium chloride was an ordinary fluid.

Administration to Animals

The same procedure as in Example 1 was repeated except that the mixed solution and the aqueous solution of calcium chloride were also administered in the following manner.

Administration of Mixed Solution and Aqueous Solution of Calcium Chloride

The aqueous solution of calcium chloride was administered first and then the mixed solution was administered. Administration in this manner forms in the living organism of a Japanese white rabbit the fibrosis-causing agent composed of sodium alginate, platelet-rich plasma (PRP), and calcium chloride. The thus formed fibrosis-causing agent takes on a gel form.

By way of the catheter, the aqueous solution of calcium chloride (0.5 mL), the mixed solution (1.0 mL), and air (10 mL) were infused sequentially. This step was repeated once again. In other words, the aqueous solution of calcium chloride (0.5 mL), the mixed solution (1.0 mL), and air (10 mL) were infused sequentially in the order listed. Incidentally, the infusion of the aqueous solution of calcium chloride, mixed solution, and air was coincident with inspiration.

Comparative Example 1

Experiments were carried out in which the fibrosis inducer is sodium alginate alone.

Preparation of Aqueous Solution of Sodium Alginate

The same procedure as in Example 1 was repeated to prepare the aqueous solution of sodium alginate.

Administration to Animals

The same procedure as in Example 1 was repeated except that the aqueous solution of sodium alginate was administered in the following manner.

Administration of Aqueous Solution of Sodium Alginate

By way of the catheter, the aqueous solution of sodium alginate (0.5 mL each) was infused twice, air (10 mL) was infused, the aqueous solution of sodium alginate (0.5 mL each) was infused twice again, and finally air (10 mL) was infused. Incidentally, the infusion of the aqueous solution of sodium alginate and air was coincident with inspiration.

Comparative Example 2

Experiments were carried out in which the fibrosis promoter is platelet-rich plasma (PRP) alone.

(Preparation of Platelet-Rich Plasma (PRP))

The same procedure as in Example 1 was repeated to prepare platelet-rich plasma (PRP).

Administration to Animals

The same procedure as in Example 1 was repeated except that the platelet-rich plasma (PRP) was administered in the following manner.

Administration of Platelet-Rich Plasma (PRP)

By way of the catheter, the platelet-rich plasma (PRP) (0.5 mL each) was infused twice, air (10 mL) was infused, the platelet-rich plasma (PRP) (0.5 mL each) was infused twice again, and finally air (10 mL) was infused. Incidentally, the infusion of the platelet-rich plasma and air was coincident with inspiration.

Comparative Example 3

Experiments were carried out in which the fibrosis promoter is platelet-rich plasma (PRP) and the gelling agent for platelet-rich plasma (PRP) is calcium chloride in the form of aqueous solution.

Preparation of Platelet-Rich Plasma (PRP) and Aqueous Solution of Calcium Chloride The same procedure as in Example 1 was repeated to prepare platelet-rich plasma (PRP), and the same procedure as in Example 2 was repeated to prepare an aqueous solution of calcium chloride.

Preparation of Mixed Solution

A mixed solution was prepared from the platelet-rich plasma (PRP) and the aqueous solution of calcium chloride which were mixed together in a ratio of 9:1 (by volume). The resulting mixed solution was a viscous liquid.

Administration to Animals

The same procedure as in Example 1 was repeated except that the mixed solution was administered in the following manner.

Administration of Mixed Solution

By way of the catheter, the mixed solution (0.5 mL each) was infused twice, air (10 mL) was infused, the mixed solution (0.5 mL each) was infused twice again, and finally air (10 mL) was infused. Incidentally, the infusion of the mixed solution and air was coincident with inspiration.

Comparative Example 4

Experiments were carried out in which the fibrosis inducer is sodium alginate and the gelling agent for platelet-rich plasma (PRP) is calcium chloride.

Preparation of Aqueous Solution of Sodium Alginate and Aqueous Solution of Calcium Chloride The same procedure as in Example 1 was repeated to prepare the aqueous solution of sodium alginate. The same procedure as in Example 2 was repeated to prepare the aqueous solution of calcium chloride.

Administration to Animals

The same procedure as in Example 1 was repeated except that the aqueous solution of sodium alginate and the aqueous solution of calcium chloride were administered in the following manner.

Administration of Aqueous Solution of Sodium Alginate and Aqueous Solution of Calcium Chloride By way of the catheter, the aqueous solution of calcium chloride (0.5 mL), the aqueous solution of sodium alginate (1.0 mL), and air (10 mL) were infused sequentially. This step was repeated once again. In other words, the aqueous solution of calcium chloride (0.5 mL), the aqueous solution of sodium alginate (1.0 mL), and air (10 mL) were infused sequentially in the order listed. Incidentally, the infusion of the aqueous solution of calcium chloride, aqueous solution of sodium alginate, and air was coincident with inspiration.

Example 3

Experiments for fibrosis were carried out in which the fibrosis inducer is iron alginate and the fibrosis promoter is platelet-rich plasma (PRP). These components were used in combination with calcium chloride as the PRP gelling agent.

Preparation of Aqueous Dispersion of Iron Alginate

An aqueous solution (1% w/v) of iron chloride was prepared by dissolving 5.0 g of iron chloride (made by Wako Pure Chemical Industries, Ltd.) in 500 mL of reverse osmosis water (RO water).

Also, an aqueous solution (1% w/v) of sodium alginate was prepared by dissolving 1.5 g of sodium alginate (made by Wako Pure Chemical Industries, Ltd.) in 150 mL of reverse osmosis water (RO water).

The aqueous solution of sodium alginate (in atomized form) was added to the aqueous solution of iron chloride being swirled, so that there was obtained iron alginate in particulate form. The aqueous dispersion of iron alginate was sifted through a sieve with an opening of 100 μm and then thoroughly washed with an aqueous solution of iron chloride. The washed iron alginate was allowed to stand overnight in an aqueous solution of iron chloride. With the supernatant removed through an aspirator, the remaining liquid was centrifuged at 500×g for three minutes. The resulting precipitates were washed with 70% ethanol three times. With the supernatant discarded, the precipitates were suspended in distilled water (made by Otsuka Pharmaceutical Co., Ltd.) one half the volume of precipitates. Thus there was obtained the aqueous dispersion of iron alginate.

(Preparation of Platelet-Rich Plasma (PRP) and Aqueous Solution of Calcium Chloride)

The same procedure as in Example 1 was repeated to prepare platelet-rich plasma (PRP), and the same procedure as in Example 2 was repeated to prepare an aqueous solution of calcium chloride.

Preparation of Fibrosis-Causing Agent

The aqueous dispersion of iron alginate and the platelet-rich plasma (PRP) were mixed together in a ratio of 1:1 (by volume). The resulting mixture was stirred to give a mixed solution. This mixed solution and the aqueous solution of calcium chloride were mixed together and stirred in a ratio of 10:1 (by volume) to give the fibrosis-causing agent. The resulting fibrosis-causing agent is in the form of gel, with iron alginate particles dispersed in the gel. Incidentally, the resulting fibrosis-causing agent was administered to animals before gelation proceeds completely after mixing with the aqueous solution of calcium chloride.

Administration to Animals

The same procedure as in Example 1 was repeated except that the fibrosis-causing agent was administered in the following manner.

Administration of Fibrosis-Causing Agent

By way of the catheter, the fibrosis-causing agent (0.6 mL each) was infused twice, air (10 mL) was infused, the fibrosis-causing agent (0.5 mL each) was infused twice again, and finally air (10 mL) was infused. Incidentally, the infusion of the fibrosis-causing agent and air was coincident with inspiration.

Comparative Example 5

Experiments were carried out in which the fibrosis inducer is iron alginate.

Preparation of Aqueous Dispersion of Iron Alginate

The same procedure as in Example 3 was repeated to prepare the aqueous dispersion of iron alginate.

Administration to Animals

The same procedure as in Example 1 was repeated except that the aqueous dispersion of iron alginate was administered in the following manner.

Administration of Aqueous Dispersion of Iron Alginate

By way of the catheter, the aqueous dispersion of iron alginate (0.5 mL each) was infused twice, air (10 mL) was infused, the aqueous dispersion of iron alginate (0.5 mL each) was infused twice again, and finally air (10 mL) was infused. Incidentally, the infusion of the aqueous dispersion of iron alginate and air was coincident with inspiration.

Example 4

Experiments for fibrosis were carried out in which the fibrosis inducer is calcium alginate and the fibrosis promoter is platelet-rich plasma (PRP). These components were used in combination with calcium chloride as the PRP gelling agent.

Preparation of Aqueous Dispersion of Calcium Alginate

An aqueous solution (1% w/v) of calcium chloride was prepared by dissolving 6.0 g of calcium chloride (made by Wako Pure Chemical Industries, Ltd.) in 600 mL of reverse osmosis water (RO water).

Also, an aqueous solution (1% w/v) of sodium alginate was prepared by dissolving 1.5 g of sodium alginate (made by Wako Pure Chemical Industries, Ltd.) in 150 mL of reverse osmosis water (RO water).

The aqueous solution of sodium alginate (in atomized form) was added to the aqueous solution of calcium chloride being swirled, so that there was obtained calcium alginate in particulate form. The aqueous dispersion of calcium alginate was sifted through a sieve with an opening of 100 μm and then thoroughly washed with an aqueous solution of calcium chloride. The washed calcium alginate was allowed to stand overnight in an aqueous solution of calcium chloride. With the supernatant removed through an aspirator, the remaining liquid was centrifuged at 500×g for three minutes. The resulting precipitates were washed with 70% ethanol three times. With the supernatant discarded, the precipitates were suspended in distilled water one half the volume of precipitates. Thus there was obtained the aqueous dispersion of calcium alginate, having 100 μm or smaller particle diameter (average particle diameter: 89 μm). Incidentally, the average particle diameter was measured by using the LS particle size distribution measuring apparatus (Beckman Coulter).

Preparation of Platelet-Rich Plasma (PRP) and Aqueous Solution of Calcium Chloride The same procedure as in Example 1 was repeated to prepare platelet-rich plasma (PRP), and the same procedure as in Example 2 was repeated to prepare an aqueous solution of calcium chloride.

Preparation of Fibrosis-Causing Agent

The aqueous dispersion of calcium alginate and the platelet-rich plasma (PRP) were mixed together in a ratio of 1:1 (by volume). The resulting mixture was stirred to give a mixed solution. This mixed solution and the aqueous solution of calcium chloride were mixed together and stirred in a ratio of 10:1 (by volume) to give the fibrosis-causing agent. The resulting fibrosis-causing agent is in the form of gel, with calcium alginate particles dispersed in the gel. Incidentally, the resulting fibrosis-causing agent was administered to animals before gelation proceeds completely after mixing with the aqueous solution of calcium chloride.

Administration to Animal

The same procedure as in Example 1 was repeated except that the fibrosis-causing agent was administered in the following manner.

Administration of Fibrosis-Causing Agent

By way of the catheter, the fibrosis-causing agent (0.6 mL each) was infused twice, air (10 mL) was infused, the fibrosis-causing agent (0.5 mL each) was infused twice again, and finally air (10 mL) was infused. Incidentally, the infusion of the fibrosis-causing agent and air was coincident with inspiration.

Table 1 below summarizes the fibrosis-causing agents prepared in Examples 1 to 4 and Comparative Examples 1 to 5.

The specimens were pathologically examined under an optical microscope for fibrosis and granulomatous inflammation in lung tissues. The specimens' optical photomicrographs taken one week or four weeks after administration are shown in FIGS. 1A to 8C, which are arranged in the order of Examples 1 and 2, Comparative Examples 1 to 4, Example 3, and Comparative Example 5.

TABLE 1

| | Fibrosis-causing Agent* | | | | Dosage (mL) | | | Form of |
| | Fibrosis Inducer | Fibrosis Promoter | Adjuvant | Method of Administration | Fibrosis Inducer | Fibrosis Promoter | Adjuvant | Fibrosis-causing Agent |
|---|---|---|---|---|---|---|---|---|
| Example 1 | Alg-Na | PRP | — | Alg-Na + PRP | 1.0 | 1.0 | — | Viscous liquid |
| Example 2 | Alg-Na | PRP | $CaCl_2$ | $CaCl_2$ → Alg-Na + PRP | 1.0 | 1.0 | 1.0 | Gel |
| Comparative Example 1 | Alg-Na | — | — | Alg-Na | 2.0 | — | — | Viscous liquid |
| Comparative Example 2 | — | PRP | — | PRP | — | 2.0 | — | Liquid |
| Comparative Example 3 | — | PRP | $CaCl_2$ | PRP + $CaCl_2$ | — | 1.8 | 0.2 | Gel |
| Comparative Example 4 | Alg-Na | — | $CaCl_2$ | $CaCl_2$ → Alg-Na | 2.0 | — | 1.0 | Gel |
| Example 3 | Alg-Fe | PRP | $CaCl_2$ | Alg-Fe + PRP + $CaCl_2$ | 1.0 | 1.0 | 0.2 | Gel + Particles |
| Comparative Example 5 | Alg-Fe | — | — | Alg-Fe | 2.0 | — | — | Particles |
| Example 4 | Alg-Ca | PRP | $CaCl_2$ | Alg-Ca + PRP + $CaCl_2$ | 1.0 | 1.0 | 0.2 | Gel + Particles |

*Alg-Na: Sodium alginate
Alg-Fe: Iron alginate
Alg-Ca: Calcium alginate
PRP: Platelet-rich plasma
$CaCl_2$: Calcium chloride Evaluation The effect of administrations to animals in Examples 1 to 4 and Comparative Examples 1 to 5 was evaluated in the following manner.

One week or four weeks after administration, the Japanese white rabbit was given an anesthetic by intravenous injection through its auricular vein. The anesthetic is somnopentyl (sodium pentobarbiturate) diluted twice with physiological saline, and its dosage is 45 mg/kg (1 mL/kg).

The Japanese white rabbit under anesthesia underwent laparotomy in dorsal position. Then, it underwent perfusion through the heart with physiological saline (containing heparin, 10 units/mL, 100 mL/head), so that it was killed by bleeding from the abdominal aorta. Finally, it had its lung extracted. Into the extracted lung was injected (at a water-gauge pressure of 25 cm) 10% buffered formalin as a preserving and fixing solution for pathologic tissues (which contains, in 100 mL, 10 mL of formalin (35 to 38% aqueous solution of formaldehyde), 0.4 g of sodium dihydrogenphosphate, and 0.65 g of sodium monohydrogenphosphate anhydride, with the rest being purified water). For immersion fixation, the lung was allowed to stand for 24 hours in the 10% buffered formalin. Subsequently, specimens were prepared by paraffin embedding and staining with hematoxyline-eosin (HE stain) and masson trichrome (MT stain).

Fibrosis

Fibrosis can be judged from the presence or absence of the appearance of fibrocytes and the deposition of extracellular organs. The rating of fibrosis was given according to the following criteria.

−: Specimens show no fibrosis.
±: Specimens show fibrosis at 1 place.
+: Specimens show fibrosis at 2 to 4 places.
++: Specimens show fibrosis at 5 to 9 places.
+++: Specimens show fibrosis at 10 places or more.

Granulomatous Inflammation

Granulomatous inflammation can be identified from the presence or absence of focal lesion due to hyperplasia of macrophages, multinucleated giant cells, lymphocytes, and fibrous tissues. The rating of granulomatous inflammation was given according to the following criteria. Incidentally, granulomatous inflammation leads to fibrosis.

−: Specimens show no granulomatous inflammation.
±: Specimens show granulomatous inflammation at 1 place.
+: Specimens show granulomatous inflammation at 2 to 4 places.
++: Specimens show granulomatous inflammation at 5 to 9 places.
+++: Specimens show granulomatous inflammation at 10 places or more.

TABLE 2

| | | One week | | Four weeks | |
| | Fibrosis-causing Agent* | Fibrosis | Granulomatous inflammation | Fibrosis | Granulomatous inflammation |
|---|---|---|---|---|---|
| Example 1 | Alg-Na + PRP | − | ++ | − | + |
| Example 2 | $CaCl_2$ → Alg-Na + PRP | ++ | ++ | ++ | ++ |
| Comparative Example 1 | Alg-Na | ± | + | − | − |

TABLE 2-continued

|  | Fibrosis-causing Agent* | One week | | Four weeks | |
|  |  | Fibrosis | Granulomatous inflammation | Fibrosis | Granulomatous inflammation |
|---|---|---|---|---|---|
| Comparative Example 2 | PRP |  |  | − | − |
| Comparative Example 3 | PRP + CaCl$_2$ | − | − |  |  |
| Comparative Example 4 | CaCl$_2$ → Alg-Na | + | ++ | + | − |
| Example 3 | Alg-Fe + PRP + CaCl$_2$ | ++ | ++ | + | + |
| Comparative Example 5 | Alg-Fe | − | + | + | − |
| Example 4 | Alg-Ca + PRP + CaCl$_2$ | +++ | +++ | +++ | +++ |

*Alg-Na : Sodium alginate
Alg-Fe : Iron alginate
Alg-Ca : Calcium alginate
PRP: Platelet-rich plasma
CaCl$_2$: Calcium chloride The results shown in Table 2 indicate that the fibrosis-causing agents pertaining to Examples 1 to 4 promote fibrosis or granulomatous inflammation (prestage thereof) in lungs. They also indicate that the fibrosis-causing agents pertaining to Comparative Examples 1 to 5 bring about neither fibrosis nor granulomatous inflammation in lungs, or they produce only limited effects.

To be more specific, it was found that the fibrosis-causing agent of Example 1 caused almost no fibrosis but remarkably caused granulomatous inflammation one week and four weeks after administration (FIGS. 1A to 1D). The noticeable granulomatous inflammation suggests the possibility of fibrosis occurring in extended periods. The fact that the effect decreases after one week or four weeks is probably due to individual differences.

Figure 2A:
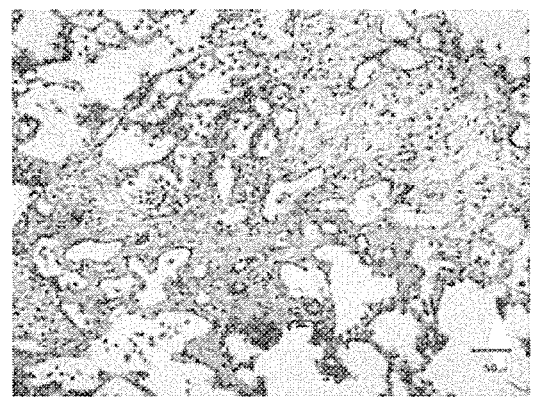
FIG. 2A is an optical photomicrograph (×200, HE-stained) showing fibrosis in lung tissues of a Japanese white rabbit, which was taken one week after administration of a fibrosis-causing agent pertaining to Example 2.
Figure 2B:
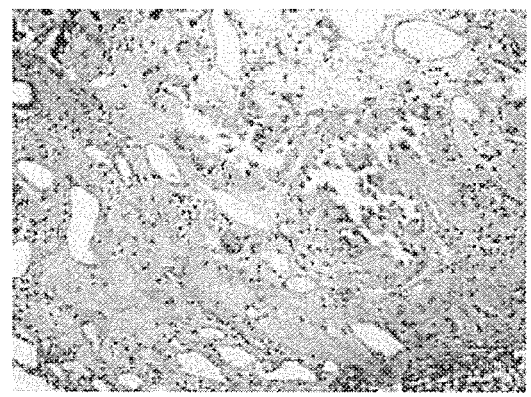
FIG. 2B is an optical photomicrograph (×200, HE-stained) showing fibrosis in lung tissues of a Japanese white rabbit, which was taken four weeks after administration of the fibrosis-causing agent pertaining to Example 2.
Figure 2C:
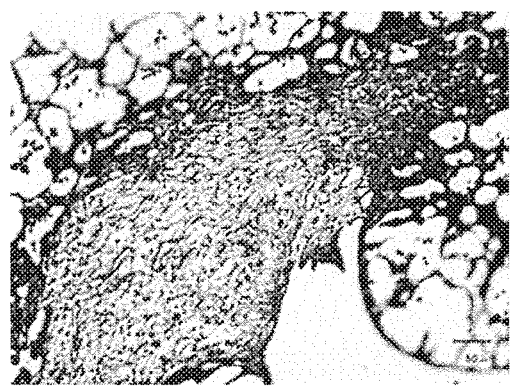
FIG. 2C is an optical photomicrograph (×200, MT-stained) showing fibrosis in lung tissues of a Japanese white rabbit, which was taken one week after administration of the fibrosis-causing agent pertaining to Example 2.
Figure 2D:
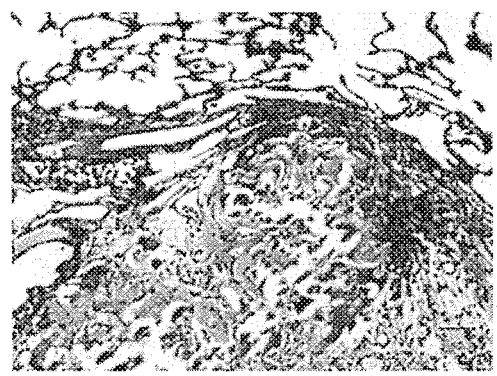
FIG. 2D is an optical photomicrograph (×200, MT-stained) showing fibrosis in lung tissues of a Japanese white rabbit, which was taken four weeks after administration of the fibrosis-causing agent pertaining to Example 2.
Figure 2E:
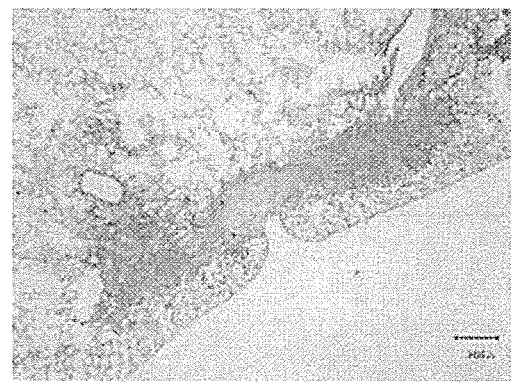
FIG. 2E is an optical photomicrograph (×100, HE-stained) showing granulomatous inflammation in lung tissues of a Japanese white rabbit, which was taken one week after administration of the fibrosis-causing agent pertaining to Example 2.
Figure 2F:
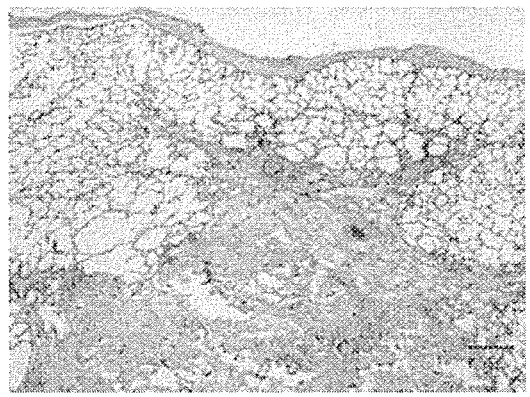
FIG. 2F is an optical photomicrograph (×100, HE-stained) showing granulomatous inflammation in lung tissues of a Japanese white rabbit, which was taken four weeks after administration of the fibrosis-causing agent pertaining to Example 2.

The fibrosis-causing agent of Example 2 is more effective than that of Example 1 on account of combination with PRP gelling agent (calcium chloride). In other words, noticeable fibrosis was observed after one week and four weeks (FIGS. 2A to 2D). More noticeable granulomatous inflammation than in Example 1 was also observed after one week and four weeks (FIGS. 2E and 2F). This enhanced effect is probably due to the addition of the gelling agent which makes the fibrosis-causing agent less fluid in the lung, permitting it to stay longer on cells.

Figure 3A:
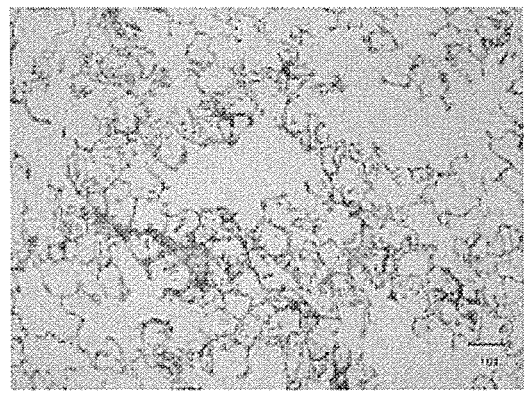
FIG. 3A is an optical photomicrograph (×200, HE-stained) showing fibrosis in lung tissues of a Japanese white rabbit, which was taken one week after administration of a fibrosis-causing agent pertaining to Comparative Example 1.
Figure 3B:
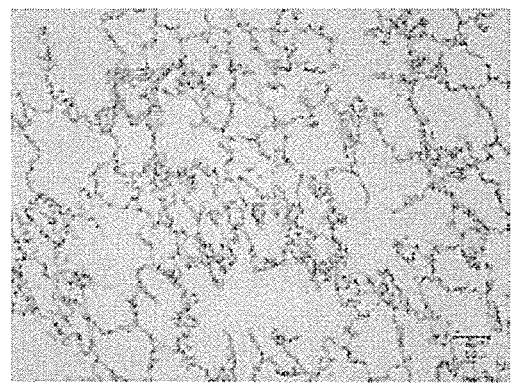
FIG. 3B is an optical photomicrograph (×200, HE-stained) showing fibrosis in lung tissues of a Japanese white rabbit, which was taken four weeks after administration of the fibrosis-causing agent pertaining to Comparative Example 1.
Figure 3C:
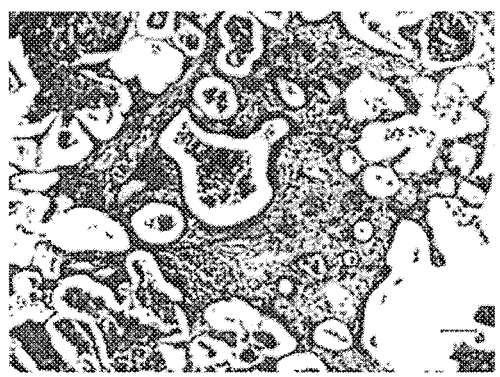
FIG. 3C is an optical photomicrograph (×200, MT-stained) showing fibrosis in lung tissues of a Japanese white rabbit, which was taken one week after administration of the fibrosis-causing agent pertaining to Comparative Example 1.
Figure 3D:
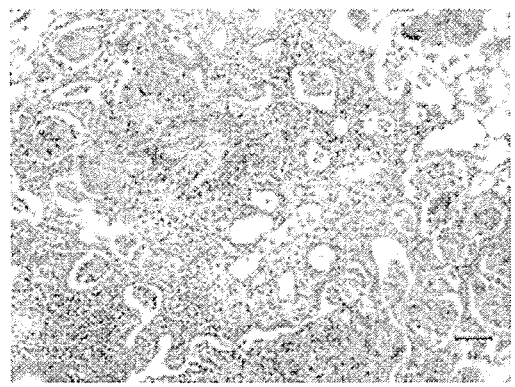
FIG. 3D is an optical photomicrograph (×200, HE-stained) showing granulomatous inflammation in lung tissues of a Japanese white rabbit, which was taken one week after administration of the fibrosis-causing agent pertaining to Comparative Example 1.

The results in Comparative Examples 1 and 4 indicate that sodium alginate has almost no effect on fibrosis (FIGS. 3A to 3C) although it is slightly effective on granulomatous inflammation (FIG. 3D). The combination of sodium alginate and PRP gelling agent merely produces limited effects (FIGS. 6A to 6E).

Figure 4:
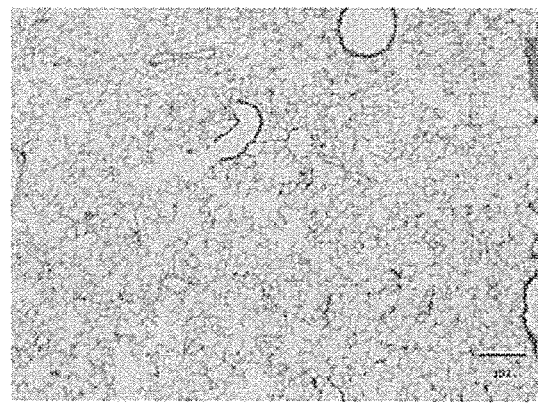
FIG. 4 is an optical photomicrograph (×40, HE-stained) showing fibrosis in lung tissues of a Japanese white rabbit, which was taken four weeks after administration of a fibrosis-causing agent pertaining to Comparative Example 2.
Figure 5:
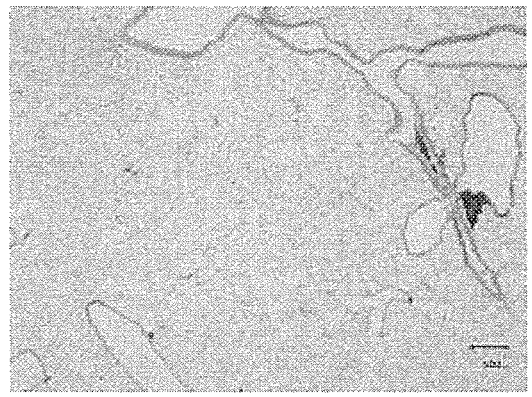
FIG. 5 is an optical photomicrograph (×40, HE-stained) showing fibrosis in lung tissues of a Japanese white rabbit, which was taken one week after administration of a fibrosis-causing agent pertaining to Comparative Example 3.
Figure 6A:
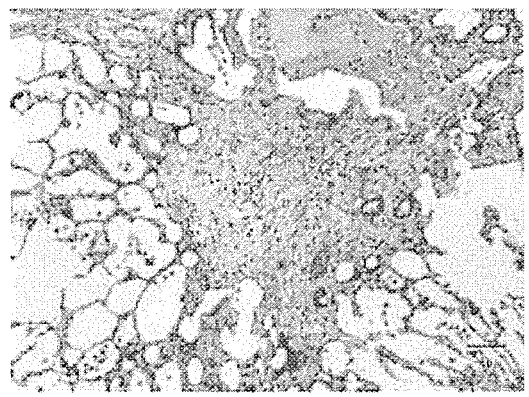
FIG. 6A is an optical photomicrograph (×200, HE-stained) showing fibrosis in lung tissues of a Japanese white rabbit, which was taken one week after administration of a fibrosis-causing agent pertaining to Comparative Example 4.
Figure 6B:
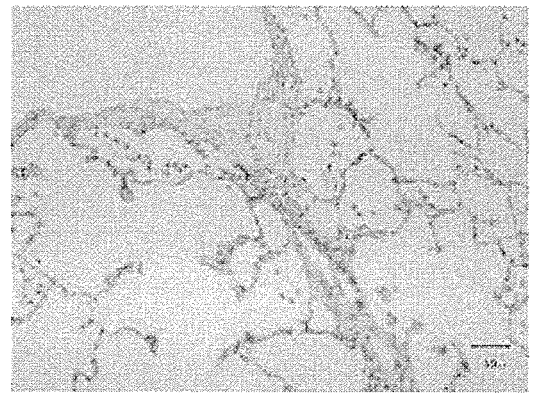
FIG. 6B is an optical photomicrograph (×200, HE-stained) showing fibrosis in lung tissues of a Japanese white rabbit, which was taken four weeks after administration of the fibrosis-causing agent pertaining to Comparative Example 4.
Figure 6C:
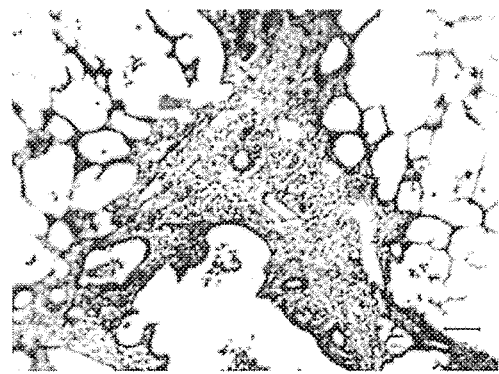
FIG. 6C is an optical photomicrograph (×200, MT-stained) showing fibrosis in lung tissues of a Japanese white rabbit, which was taken one week after administration of the fibrosis-causing agent pertaining to Comparative Example 4.
Figure 6D:
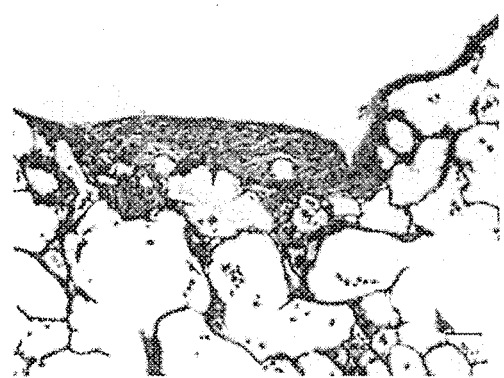
FIG. 6D is an optical photomicrograph (×200, MT-stained) showing fibrosis in lung tissues of a Japanese white rabbit, which was taken four weeks after administration of the fibrosis-causing agent pertaining to Comparative Example 4.
Figure 6E:
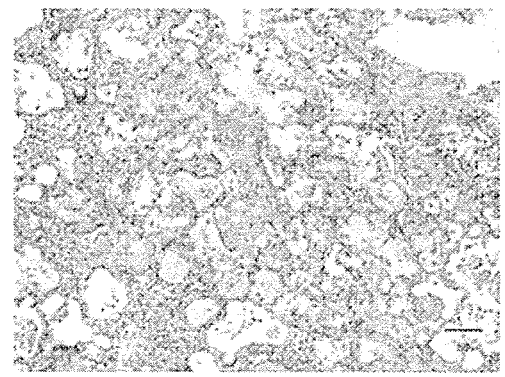
FIG. 6E is an optical photomicrograph (×200, HE-stained) showing granulomatous inflammation in lung tissues of a Japanese white rabbit, which was taken one week after administration of the fibrosis-causing agent pertaining to Comparative Example 4.
Figure 7A:
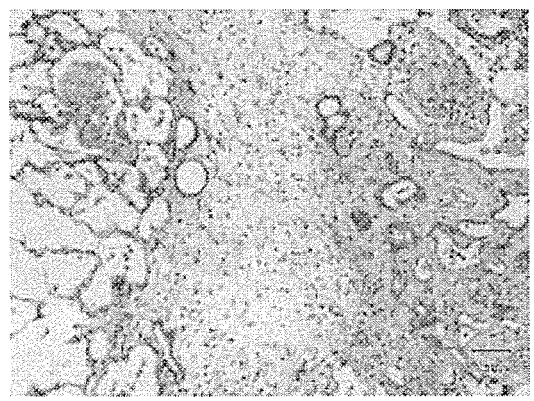
FIG. 7A is an optical photomicrograph (×200, HE-stained) showing fibrosis in lung tissues of a Japanese white rabbit, which was taken one week after administration of a fibrosis-causing agent pertaining to Example 3.
Figure 7B:
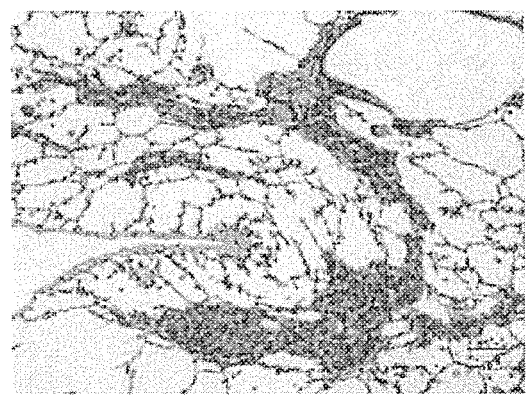
FIG. 7B is an optical photomicrograph (×200, HE-stained) showing fibrosis in lung tissues of a Japanese white rabbit, which was taken four weeks after administration of the fibrosis-causing agent pertaining to Example 3.
Figure 7C:
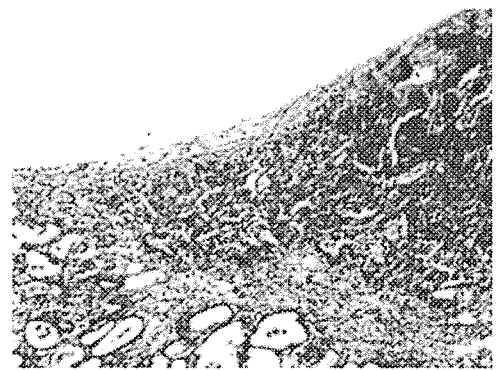
FIG. 7C is an optical photomicrograph (×200, MT-stained) showing fibrosis in lung tissues of a Japanese white rabbit, which was taken one week after administration of the fibrosis-causing agent pertaining to Example 3.
Figure 7D:
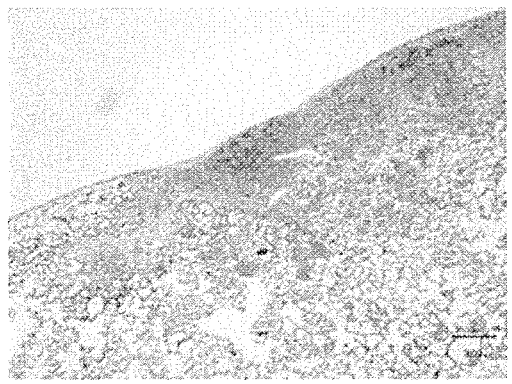
FIG. 7D is an optical photomicrograph (×100, HE-stained) showing granulomatous inflammation in lung tissues of a Japanese white rabbit, which was taken one week after administration of the fibrosis-causing agent pertaining to Example 3.
Figure 7E:
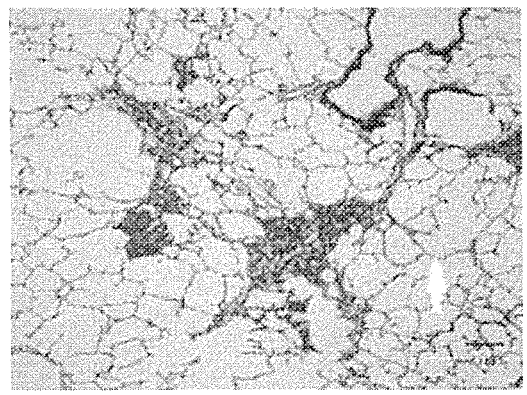
FIG. 7E is an optical photomicrograph (×100, HE-stained) showing granulomatous inflammation in lung tissues of a Japanese white rabbit, which was taken one week after administration of the fibrosis-causing agent pertaining to Example 3.
Figure 8A:
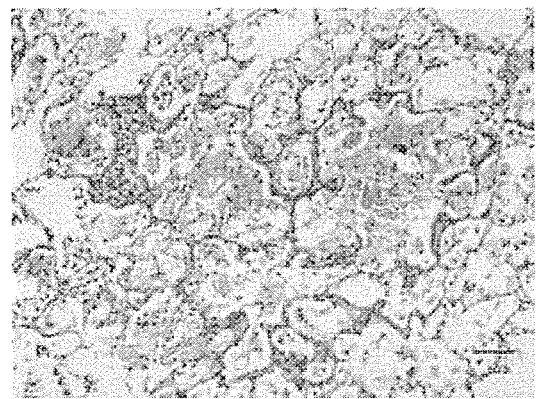
FIG. 8A is an optical photomicrograph (×200, HE-stained) showing fibrosis in lung tissues of a Japanese white rabbit, which was taken one week after administration of a fibrosis-causing agent pertaining to Comparative Example 5.
Figure 8B:
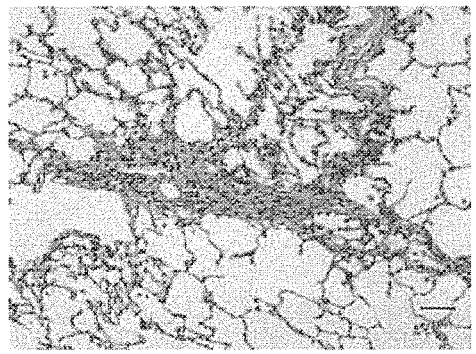
FIG. 8B is an optical photomicrograph (×200, HE-stained) showing fibrosis in lung tissues of a Japanese white rabbit, which was taken four weeks after administration of the fibrosis-causing agent pertaining to Comparative Example 5.
Figure 8C:
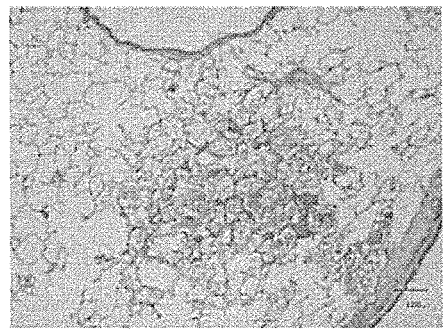
FIG. 8C is an optical photomicrograph (×100, HE-stained) showing granulomatous inflammation in lung tissues of a Japanese white rabbit, which was taken one week after administration of the fibrosis-causing agent pertaining to Comparative Example 5.

The results in Comparative Examples 2 and 3 indicate that platelet-rich plasma (PRP) induces no fibrosis (FIGS. 4 and 5).

Moreover, the results in Example 3 and Comparative Example 5 suggest that iron alginate induces fibrosis. It was also found that iron alginate used alone is not so effective (FIGS. 8A to 8C) but becomes effective when used in combination with platelet-rich plasma (PRP) and PRP gelling agent (FIGS. 7A to 7E).

The results in Example 4 apparently indicate that an extremely high effect of fibrosis is produced when calcium alginate is used in combination with platelet-rich plasma (PRP) and PRP gelling agent.

It should be understood by those skilled in the art that various modifications, combinations, sub-combinations and alterations may occur depending on design requirements and other factors insofar as they are within the scope of the appended claims or the equivalents thereof.

What is claimed is:

1. A method of causing pulmonary fibrosis for the treatment of Chronic Obstructive Pulmonary Disease (COPD) comprising administering to a patient's respiratory system, a fibrosis causing agent comprising a fibrosis inducer and a fibrosis promoter.

2. A method for causing pulmonary fibrosis for the treatment of Chronic Obstructive Pulmonary Disease (COPD) comprising administering to a subject's respiratory system a fibrosis causing agent.

3. The method according to claim 2, wherein the fibrosis causing agent comprises a fibrosis inducer and a fibrosis promoter.

4. The method according to claim 3, wherein the fibrosis promoter contains platelets or platelet-rich plasma (PRP).

5. The method according to claim 4, wherein the fibrosis promoter contains platelet-rich plasma (PRP) and a PRP gelling agent.

6. The method according to claim 5, wherein the PRP gelling agent contains at least one selected from the group consisting of calcium, calcium salt, fibrin, fibrinogen, thrombin, vitamin K, and factor X.

7. The method according to claim 2, wherein the fibrosis inducer contains at least one polyanion.

8. The method according to claim 7, wherein the polyanion is at least one selected from the group consisting of alginic acid, alginate, and alginic ester.

9. A method for treating Chronic Obstructive Pulmonary Disease (COPD) comprising administering to a patient's respiratory system, a composition comprising a fibrosis-causing agent, the fibrosis-causing agent comprising a fibrosis inducer and a fibrosis promoter.

* * * * *